United States Patent
Curtis et al.

(10) Patent No.: US 10,301,239 B2
(45) Date of Patent: May 28, 2019

(54) SYNTHESIS OF POLYOLS SUITABLE FOR CASTOR OIL REPLACEMENT

(71) Applicant: THE GOVERNORS OF THE UNIVERSITY OF ALBERTA, Edmonton (CA)

(72) Inventors: Jonathan M. Curtis, Edmonton (CA); Tolibjon S. Omonov, Edmonton (CA); Ereddad Kharraz, Edmonton (CA)

(*) Notice: Subject to any disclaimer, the term of this patent is extended or adjusted under 35 U.S.C. 154(b) by 0 days.

(21) Appl. No.: 15/748,149

(22) PCT Filed: Jul. 29, 2016

(86) PCT No.: PCT/CA2016/050895
§ 371 (c)(1),
(2) Date: Jan. 26, 2018

(87) PCT Pub. No.: WO2017/020124
PCT Pub. Date: Feb. 9, 2017

(65) Prior Publication Data
US 2018/0222829 A1    Aug. 9, 2018

Related U.S. Application Data

(60) Provisional application No. 62/199,429, filed on Jul. 31, 2015.

(51) Int. Cl.
C07C 29/03    (2006.01)
C08G 18/36    (2006.01)
(Continued)

(52) U.S. Cl.
CPC .............. *C07C 29/03* (2013.01); *C07C 29/48* (2013.01); *C07C 33/02* (2013.01); *C07D 303/16* (2013.01);
(Continued)

(58) Field of Classification Search
CPC ......... C07C 29/03; C07C 29/48; C07C 33/02; C07C 2531/04; C07C 2531/08;
(Continued)

(56) References Cited

U.S. PATENT DOCUMENTS 4,886,893 A    12/1989 Meffert et al.
6,258,869 B1    7/2001 Shah et al.
(Continued)

FOREIGN PATENT DOCUMENTS

WO    WO-2014130391 A1 * 8/2014 .......... C07D 301/19

OTHER PUBLICATIONS

Lathi, P. S., et al., Green approach for hte preparatin of biodegradable lubricant base stock from epoxidized vegetable oil, 2007, Applied Catalysis. B Environmental, vol. 69, pp. 207-212 (Year: 2007).*

(Continued)

*Primary Examiner* — Yate' K Cutliff
(74) *Attorney, Agent, or Firm* — Bennett Jones LLP

(57) ABSTRACT

A method for the preparation of polyol from an unsaturated TAG oil that can function similarly to castor oil in certain applications. The method comprises controlled epoxidation of the TAG oil with an acid and an oxidizing agent to obtain a partially epoxidized TAG oil with desired iodine and oxirane values; hydroxylating the partially epoxidized TAG oil using a monoalcohol and a solid acid catalyst to obtain the polyol. The resulting polyols are comprised of a triglyceride structure and hydroxyl values, viscosities, and colors that are similar to castor oil.

20 Claims, 4 Drawing Sheets

(51) Int. Cl.
 *C07C 29/48* (2006.01)
 *C07D 303/16* (2006.01)
 *C07C 33/02* (2006.01)
 *C11C 3/00* (2006.01)
 *C08G 18/62* (2006.01)
 *C08G 18/76* (2006.01)

(52) U.S. Cl.
 CPC ........... *C08G 18/36* (2013.01); *C08G 18/627* (2013.01); *C08G 18/7664* (2013.01); *C11C 3/006* (2013.01); *C07C 2531/04* (2013.01); *C07C 2531/08* (2013.01)

(58) Field of Classification Search
 CPC ......... C07C 67/31; C11C 3/006; C08G 18/36; C07D 303/02
 See application file for complete search history.

(56) References Cited

U.S. PATENT DOCUMENTS

| | | | |
|---|---|---|---|
| 6,548,609 | B2 | 4/2003 | Ramirez-de-Arellano-Aburto et al. |
| 6,686,435 | B1 | 2/2004 | Petrovic et al. |
| 7,674,925 | B2 | 3/2010 | Garrett et al. |
| 7,960,444 | B2 | 6/2011 | Lysenko et al. |
| 7,973,187 | B2 | 7/2011 | Luo et al. |
| 8,058,470 | B2 | 11/2011 | Uyama et al. |
| 8,097,739 | B2 | 1/2012 | Luo et al. |
| 8,178,714 | B2 | 5/2012 | Awang et al. |
| 8,471,072 | B2 | 6/2013 | Suppes et al. |
| 8,692,030 | B1 | 4/2014 | Ionescu et al. |
| 9,035,105 | B2 | 5/2015 | Reese et al. |
| 9,216,940 | B2 | 12/2015 | Curtis et al. |
| 2003/0088054 | A1 | 5/2003 | Chasar et al. |
| 2006/0041156 | A1 | 2/2006 | Casper et al. |
| 2007/0123725 | A1 | 5/2007 | Lorenz |
| 2007/0155934 | A1 | 7/2007 | Waidner et al. |
| 2008/0262259 | A1 | 10/2008 | Luo et al. |
| 2008/0293913 | A1 | 11/2008 | Abu Hassan et al. |
| 2010/0217022 | A1* | 8/2010 | Abraham ............... C08G 18/36 554/163 |
| 2010/0261805 | A1* | 10/2010 | Abraham ............... C08G 18/36 521/170 |
| 2010/0311992 | A1 | 12/2010 | Petrovic et al. |
| 2011/0015293 | A1 | 1/2011 | Ma et al. |
| 2011/0118432 | A1 | 5/2011 | Zhao et al. |
| 2012/0022186 | A1 | 1/2012 | Craun et al. |
| 2012/0041089 | A1 | 2/2012 | Roh et al. |
| 2012/0136169 | A1 | 5/2012 | Abraham et al. |
| 2013/0005937 | A1* | 1/2013 | Cramail ................. C07C 67/03 528/85 |
| 2013/0131302 | A1* | 5/2013 | Suppes ................ C07C 29/147 528/85 |
| 2013/0274494 | A1* | 10/2013 | Curtis .................... C07C 67/31 554/172 |
| 2014/0275310 | A1 | 9/2014 | Adkins et al. |
| 2015/0240050 | A1 | 8/2015 | Rao et al. |
| 2015/0337112 | A1 | 11/2015 | Ghosh-Dastidar et al. |

OTHER PUBLICATIONS

Dai et al.—Synthesis and Characterization of the Different Soy-Based Polyols, JAOCS (2009) 86:261-267.

Guo et al., Hydrolysis of Epoxidized Soybean Oil in the Presence of Phosphoric Acid, JAOCS (2007) 84:929.

Guo et al., Structure and Properties of Halogenated and Nonhalogenated Soy-Based Polyols, Polym. Sci.: Part A: Polym. Chem, vol. 38, 3900-3910 (2000).

Ionescu et al., Ethoxylated Soybean Polyols for Polyurethanes, J Polym Environ (2010) 18:1-7.

* cited by examiner

SYNTHESIS OF POLYOLS SUITABLE FOR CASTOR OIL REPLACEMENT

FIELD OF THE INVENTION

The present invention relates to a process for the preparation of polyols from unsaturated triacylglycerol oils, which polyols may have properties similar to castor oil.

BACKGROUND OF THE INVENTION

Castor oil is a vegetable oil obtained by pressing the seeds of the castor oil plant *Ricinus communis*. Worldwide castor oil production is estimated to be about 0.9 million metric tons per year, with a large proportion being produced in India, China, and Brazil. Castor oil comprises triacylglyceride polyols, having unsaturated and hydroxylated fatty acids, and as such it may be used to manufacture polyurethanes, cosmetics, lubricants, surfactants, greases, coatings, inks, personal care goods, detergents, oleochemicals, and the like. Castor oil is a renewable bio-based product, but suffers from large fluctuations in supply and price. Castor beans also contains ricin which is highly toxic to humans and animals.

In polymer chemistry and materials science, polyols are chemical compounds with multiple hydroxyl functional groups available for chemical reactions. A major use of polyols is as a reactant to make polymers. Polyols may also be used for other purposes including in cosmetic formulations, lubricants and as chemical intermediates. Polyols themselves may be monomeric or oligomeric.

Polyol production from renewable, non-petroleum based sources is desirable from a sustainability perspective. Methods are known for the preparation of polyols from vegetable oil, however, such methods typically involve harsh reaction conditions that are not easily controlled, and typically involve expensive starting materials and catalysts. Unsaturated natural oils or fatty acids may be oxidized via ozonolysis, or epoxidized with peroxy acids, followed by hydroxylation with nucleophiles.

It may be desirable to produce polyols having properties similar to castor oil from naturally sourced oils, which may allow for castor oil replacement or other industrial use, while mitigating the disadvantages of the prior art.

SUMMARY OF THE INVENTION

The invention comprises a process for the preparation of polyols from unsaturated triacylglycerol oil, which polyols have properties similar to castor oil. The polyols comprise a triacylglycerol backbone and three fatty acid residues, and which may comprise at least one carbon-carbon double bond and at least one hydroxyl group. One specific preferred polyol has the structure of Formula I:

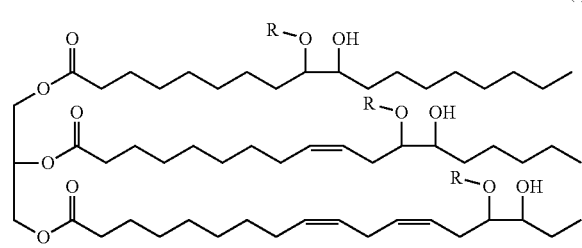

(I)

The resulting polyol composition will comprise a blend of different polyol structures, each having a number of double-bonds and hydroxyl groups. Reference to the properties of the resulting polyols will be a reference to a bulk composition of polyol.

In one aspect, the invention comprises a method of producing polyols from an unsaturated triacylglycerol (TAG) oil, comprising the steps of:

(a) partially epoxidizing the unsaturated TAG oil with an acid and an oxidizing agent to obtain a partially epoxidized TAG oil which is still unsaturated; and (b) hydroxylating the partially epoxidized TAG oil using an alcohol and an acid catalyst to obtain hydroxylated and unsaturated TAG polyols.

Preferably, the acid catalyst comprises a heterogenous acid catalyst.

In another aspect, the invention may comprise a composition comprising hydroxylated and unsaturated TAG polyols, wherein the composition has a hydroxyl value of between about 110 mg KOH/g to about 210 mg KOH/g, preferably between about 150 mg KOH/g to about 200 mg KOH/g, and a viscosity which ranges from about 0.4 Pa·s to about 2.5 Pa·s, preferably from about 0.6 Pa·s to about 1.6 Pa·s. In one embodiment, the polyol is light yellow in colour.

In one embodiment, the polyols comprise no more than about 15% non-monomeric polyols, and preferably less than about 10%. In one embodiment, less than about 7% of the polyols are non-monomeric, the non-monomeric portion being substantially all dimers. The polyols may be substantially free of trimer or higher oligomers.

In one embodiment, the unsaturated TAG oil comprises camelina oil, canola oil, high oleic canola oil, sunflower oil, juvenile canola oil, flaxseed oil, camelina oil, solin oil, yellow mustard oil, brown mustard oil, oriental mustard oil, palm oil olein, palm oil, soy oil, high erucic acid rapeseed oil, hemp oil, safflower oil, corn oil, olive oil, cottonseed oil, peanut oil, nut oils, algal oils, fish oils or mixtures thereof. In one embodiment, the unsaturated TAG oil comprises camelina oil. In one embodiment, the unsaturated TAG oil comprises a mixture of oils. In one embodiment, the unsaturated fatty acid comprises a mixture of camelina oil and flaxseed oil.

In one embodiment, the acid used in the epoxidation step comprises formic acid or acetic acid and the oxidizing agent comprises hydrogen peroxide. In one embodiment, the TAG oil is mixed with the oxidizing agent at a temperature of between about 20° to about 40°, and preferably about 30° C. In one embodiment, the temperature is gradually increased to about 40° to about 80°, preferably about 60° C., during or after addition of the acid. In one embodiment, the partially epoxidized TAG oil is extracted using an organic solvent and dried. In one embodiment, the partially epoxidized TAG oil is washed with water and dried without the use of a solvent.

In one embodiment, the acid catalyst is added to a mixture of the partially epoxidized TAG oil and a monoalcohol at a temperature of between about 40° C. to about 80° C., preferably at about 60° C. In one embodiment, the acid catalyst comprises a heterogeneous macroreticular ion exchange resin. In one embodiment, the ratio of monoalcohol to the partially epoxidized TAG oil ranges from between about 1:0.3 to about 1:1 by weight. In one embodiment, the monoalcohol comprises methanol or ethanol. In one embodiment, hydroxylation is conducted for between about 3.0 hours to about 24 hours, preferably from about 3.0 hours to about 12 hours, more preferably from about 3.0 hours to about 5.0 hours. In one embodiment, the excess alcohol is then removed by distillation, low pressure evaporation or other similar process.

In other aspects, the invention may comprise a polymer and methods of making a polymer comprising crosslinked polyols as described and claimed herein.

BRIEF DESCRIPTION OF THE DRAWINGS

The following drawing forms part of the specification and is included to further demonstrate certain embodiments or various aspects of the invention. In some instances, embodiments of the invention can be best understood by referring to the accompanying drawing in combination with the detailed description presented herein. The description and accompanying drawing may highlight a certain specific example, or a certain aspect of the invention. However, one skilled in the art will understand that portions of the example or aspect may be used in combination with other examples or aspects of the invention

DETAILED DESCRIPTION OF PREFERRED EMBODIMENTS

The present invention relates to a process for the preparation of polyols from an unsaturated TAG oil, which polyols have properties similar to castor oil, permitting replacement for castor oil in various applications. An unsaturated TAG oil is subjected to controlled partial epoxidization and hydroxylation to yield a polyol composition having triaclyglycerides which retain sufficient degree of unsaturation (for example, as measured by iodine value) so that these polyols have a similar viscosity to that of castor oil, and a similar degree of hydroxylation (for example, as measured by hydroxyl value) compared to castor oil. Such parameters are significant for various applications of castor oil or of other polyols, and the ability to optimize these parameters may be advantageous.

Generally, the polyols of the present invention comprise monomeric triacylglyceride structures, comprising alkoxylated and unsaturated fatty acid moieties bearing hydroxyl functional groups. As used herein, a composition comprising polyols is similar to castor oil if the polyols exhibit at least one property similar to castor oil, such that the polyols are the functional equivalent of castor oil in respect of that property. While certain embodiments of the present invention may be directed to polyols intended to replace castor oil in certain applications, the polyols of the present invention may be prepared with specific properties which may permit use for any application regardless of whether or not such polyols are considered a replacement for castor oil, or actually used as a replacement for castor oil.

In one embodiment, the method of the present invention comprises a method of producing polyols from an unsaturated triacylglyceride (TAG) oil, comprising the steps of:

(a) partially epoxidizing the unsaturated TAG oil with an acid and an oxidizing agent under controlled conditions to obtain a partially epoxidized TAG oil which is still unsaturated; and (b) hydroxylating the partially epoxidized TAG oil using an alcohol and an acid catalyst to obtain hydroxylated and unsaturated TAG polyols.

Manipulation of the parameters of steps (a) and (b) allow for considerable variations in the final distribution of polyol structures. Such parameters may include, but are not limited to, the degree of unsaturation of the starting TAG oil and the choice of reactants. The viscosity, shape and polarity of the resulting polyol structures may be varied by using different ring opening alcohols, dialcohols, acids, amines or other reactants capable of donating a proton.

Figure 1:
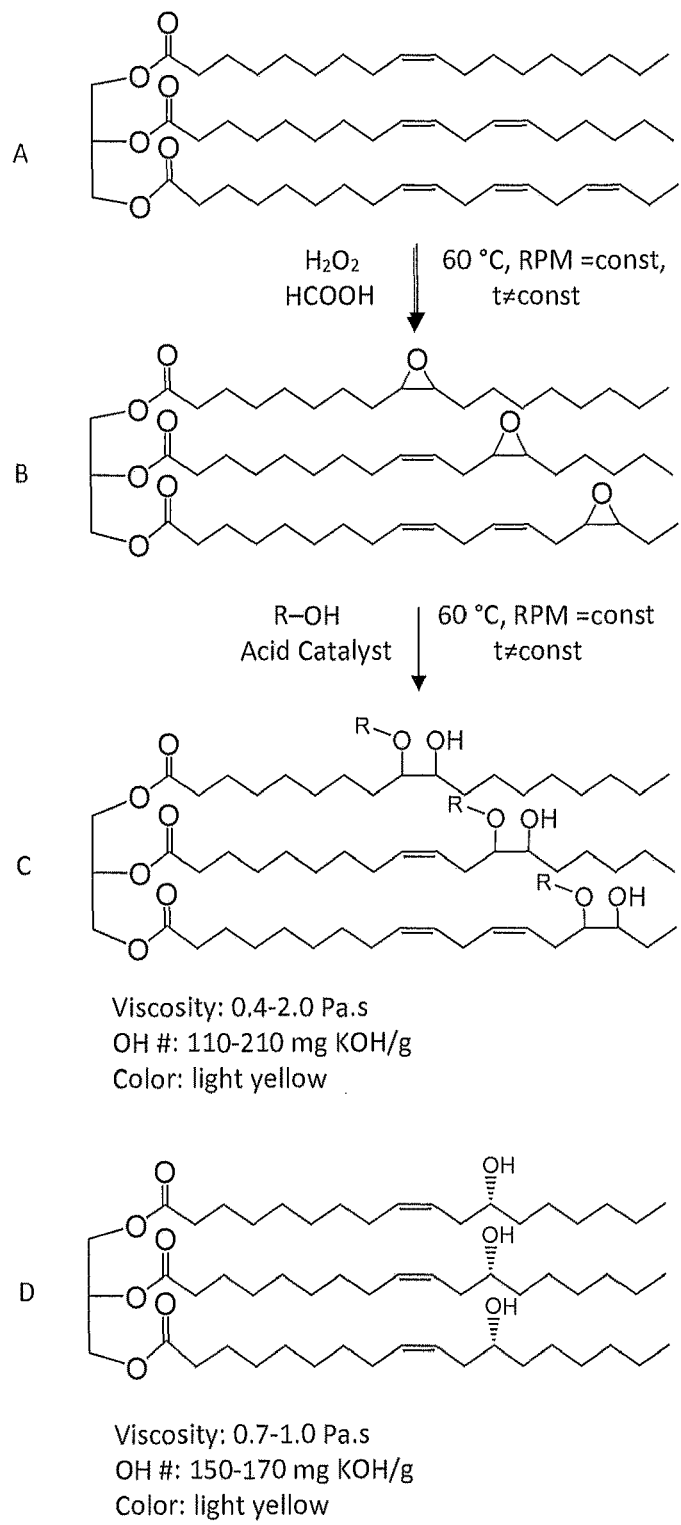
FIG. 1 shows one embodiment of the process of the present invention, where A=conceptual structure of an unsaturated TAG oil, B=conceptual structure of a partially epoxidized TAG oil, C=conceptual structure of a resulting polyol (alkoxylated and hydroxylated TAG oil), D=conceptual structure of a castor oil TAG, and compares the hydroxyl values (OHV, mg KOH/g), viscosities, and colors of the produced polyol with castor oil.

FIG. 1 shows a schematic of one embodiment of a process of the present invention. The unsaturated TAG oil comprises triglycerides having unsaturated fatty acid chains, such as those found in refined or partially refined vegetable oils. Many unsaturated oils can be used as the starting material, however those oils with higher degrees of unsaturation, such as canola oil, high oleic canola oil, sunflower oil, flaxseed oil, solin oil, yellow mustard oil, brown mustard oil and oriental mustard oil, palm oils, fractionated oils for example, palm oil olein, hemp oil or camelina oil, are preferred. Edible oils which are fully refined, (for example, degummed, bleached, deodorised) can be used as can non-refined oils that may not be food grade, such as juvenile or "green" canola oil, camelina oil, or high erucic acid rapeseed oil. Unsaturated triglyceride oil may also be sourced from algal oil, or certain animal oil sources such as tallow or fish oils. Use of different oils with different triglyceride compositions, when partially epoxidized, will result in different polyols having different molecular weights, hydroxyl numbers, and viscosities, giving access to a wide variety of polyols for various purposes.

In one embodiment, the TAG oil comprises camelina oil, flaxseed oil, or a mixture of camelina and flaxseed oil.

The degree of unsaturation of an oil may be measured by its iodine value, also known as an iodine absorption value. The iodine value of the TAG oil used in the present invention is preferably greater than that of castor oil, which is from about 82 to about 89, as some of the unsaturated sites will be epoxidized and hydroxylated. The iodine value of camelina oil is about 127 to about 155, while the iodine value of flaxseed oil is about 160 to about 190. Therefore, in one embodiment, the unsaturated TAG oil has an iodine value greater than about 120, preferably greater than about 150.

In one embodiment, the controlled partial epoxidation step of the TAG oil involves in-situ generated performic or peracetic acid from formic acid or acetic acid with an oxidizing agent, such as hydrogen peroxide. It is not preferred to use other acids, and peroxyacids in particular are not preferred. In one embodiment, the acid is slowly added to a well-stirred emulsion of the TAG oil and hydrogen peroxide. In one embodiment, the emulsion is formed by mixing the TAG oil with hydrogen peroxide at a temperature of about 20° to about 40° C., preferably about 30° C. The temperature is gradually increased to about 40° to about 80°, preferably about 60° C., after the acid addition. The reaction may then proceed with mixing until the double bonds of the TAG oil are partially consumed. The reaction is stopped and the partially epoxidized TAG oil is extracted from the mixture by addition of an organic solvent (such as, for example, ethyl acetate) and washes of salt water. The partially epoxidized TAG oil may then be dried by addition of sodium sulfate and removal of the solvent by evaporation. In one embodiment, the partially epoxidized TAG oil is washed with water and dried by addition of sodium sulfate, without use of solvent.

The resulting partially epoxidized substrate will have some but not all of the carbon-carbon double bonds reacted to form epoxide groups. For example, camelina oil is over 90% unsaturated, and comprises approximately 16% each of the monounsaturated oleic acid (18:1n-9) and eicosenoic acid (20:1-11), as well as about 17% linoleic acid (18:2n-6) and 38% alpha-linolenic acid (18:3n-3). Therefore, on average, a camelina oil triglyceride molecule may have 5 carbon-carbon double bonds. After controlled partial epoxidation, on average three of those double bonds may have been epoxidized, leaving two double bonds intact. After controlled partial epoxidation, the partially epoxidized TAG oil may have an iodine value between about 60 to about 85, similar to that of castor oil.

In one embodiment, the amount of acid used in the epoxidation step is controlled to be less than about 1:1 molar ratio for each double bond in the TAG oil, while the oxidizing agent is present in a molar ratio greater than about 1:1. For example, the amount of acid may be calculated such that every double bond will be reacted with about 0.25 mol of acid and about 1.5 mol of oxidizing agent. In the case of camelina oil, the molar ratio of components may be about camelina oil:hydrogen peroxide:formic acid=1.0:7.5:1.25 based on a double bond functionality (amount of double bonds per TAG) of camelina oil of approximately 5. The average molecular weight of camelina oil was determined to be about 893 g/mol. Each molecule of formic acid is expected to participate in epoxidation of double bonds at least about 4 times. The reduced amount of acid slows the epoxidation reaction down, but this condition is desirable to avoid epoxy ring opening by acid and acid-generated nucleophiles. A molar excess of $H_2O_2$ is desirable to compensate the loss/decomposition of peroxide during epoxidation at elevated temperatures. It is known from the literature that the decomposition rate of $H_2O_2$ increases approximately 2.2 times for each 10° C. rise in temperature in the range from 20° C. to 100° C.

In one embodiment, the acid is added slowly in small portions, so as to limit the rate of reaction at an initial stage, again to avoid epoxy ring opening. For example, formic acid (85% aqueous solution) may be added dropwise at an addition rate of about 10 g/min (about 0.22 mol/min).

The epoxidation step may be stopped when the TAG oil reaches a desired oxirane oxygen content ("OOC", expressed as weight percent). OOC is a measure of the degree of epoxidation, and the OOC of the partially epoxidized TAG oil may be determined using conventional techniques which are well known to those skilled in the art. In one embodiment, the epoxidation step is stopped when the OOC is in the range from about 3.0% to about 6.0%, preferably between about 4.0% to about 5.5%. The final OOC value is directly related to the hydroxyl number of the final polyols, therefore, a desired hydroxyl number may be attained by controlling the final OOC value.

The epoxide rings are then hydroxylated in a ring opening step to produce the desired polyols. In one embodiment, the partially epoxidized TAG oil may be hydroxylated with an alcohol and an acid catalyst, which is preferably a heterogenous acid catalyst. In one embodiment, the ring opening step is conducted using a monoalcohol, such as methanol or ethanol. In one embodiment, an excess amount of the monoalcohol is used. In one embodiment, monoalcohols can be recovered and reused.

The hydroxylation reaction may proceed with an alcohol to partially epoxidized TAG oil ratio of greater than about 0.2:1. In order to maintain the triacylglycerol structure of the polyol and to avoid transesterification reactions, an excess amount of the alcohol is preferred in the ring-opening hydroxylation step. In one embodiment, the alcohol is a monoalcohol and is used in a ratio to the partially epoxidized TAG oil between about 1:0.3 to about 1:1 by weight. An excess amount of the monoalcohol concomitantly initiates rapid epoxy ring opening reactions at shorter periods of reaction, and acts as a solvent for the process. An excess amount of alcohol is also desirable to avoid oligomerization of epoxidized TAGs with hydroxylated TAGs.

In one embodiment, the acid catalyst comprises a heterogeneous macroreticular ion exchange resin, which may be in spherical or in bead form. Preferred properties of suitable resins include high porosity ranging from about 30% to about 50% and surface area ranging from about 45 $m^2/g$ to about 65 $m^2/g$ to expose reactive groups, and sulfonic acid functionality. Commercially available catalysts such as Amberlyst™ 15 may be suitable. It is possible to use a homogeneous (liquid) acid catalyst under conditions that avoid oligomerization. Use of a heterogeneous solid acid catalyst and an alcohol may prevent premature ring opening, which is more likely to occur with use of a homogeneous liquid acid catalyst in an aqueous medium.

Hydroxylation with a monoalcohol such as ethanol or methanol will result in a single hydroxyl group and an alkoxy group from each epoxide group. It is preferred to avoid conditions which would result in dihydroxyl group formation from a single epoxide group, such as the use of water as a ring-opening nucleophile in the presence of a strong acid.

In one embodiment, a mixture of the partially epoxidized TAG oil and the monoalcohol is heated, and the acid catalyst is added once the mixture has reached a temperature of about 40° to about 80° C., preferably about 60° C. In one embodiment, the mixture is agitated (i.e., hydroxylation is conducted) for between about 3.0 hours to about 24 hours, preferably from 3.0 hours to about 5.0 hours. Preferably, the hydroxylation period is kept to the minimum required to fully open the epoxide rings, which can be achieved by monitoring the residual oxirane content. In one embodiment, the hydroxylation step is stopped when the residual oxirane content is less than about 0.02%.

Following hydroxylation, the heterogenous catalyst may be easily replaced in the reactor or removed by filtration, eliminating the need for solvents (i.e., ethyl acetate and water) typically required for work-up and decreasing manufacturing costs. Depending upon its reactivity, the catalyst may be re-used for multiple hydroxylation cycles. The monoalcohol can be recovered by distillation, and recovered monoalcohol may be re-used for further hydroxylation processes. The color of the resulting polyol is lighter compared to polyols produced using homogeneous mineral or carboxylic acids.

In one embodiment, the resulting polyols are substantially monomeric, comprising less than about 15% non-monomeric polyols, preferably less than about 10%. In one embodiment, less than about 7% of the polyols are non-monomeric. In one embodiment, the polyols are substantially free of trimer or higher oligomers. In other words, the non-monomeric polyols are substantially all dimers.

The hydroxyl value ("OHV", expressed as mg KOH/g) of the resulting polyols may be determined using conventional techniques which are well known to those skilled in the art. In one embodiment, the OHV of the polyol ranges from about 140 mg KOH/g to about 190 mg KOH/g which is similar to the OHV of castor oil which ranges from about 150 mg KOH/g to about 170 mg KOH/g. In one embodiment, the viscosity of the polyols ranges from about 0.6 Pa·s to about 1.6 Pa·s. which is similar to the viscosity of castor oil which ranges from about 0.7 Pa·s to about 1.0 Pa·s. The light yellow color is shared by both the produced polyols and castor oil. In one embodiment, the polyols are made from a blend of TAG oils such that the polyols have a similar OHV and iodine value to castor oil, or such that it has targeted OHV and iodine values.

The polyols of the present invention may be used in manufacturing various products in the same manner as castor oil including, but not limited to, polyurethanes, cosmetics, lubricants, surfactants, greases, coatings, inks, personal care goods, detergents, oleochemicals, and the like. Manufacturing of cost-effective castor oil replacement polyols from industrial plant oils may cover the need for imported castor oil and castor oil based oleochemicals, thereby supporting local oilseed producers and farmers. The castor oil replacement may confer greater stability in the supply of bio-based hydroxylated oils for industrial use.

Polyurethanes (PU) may be produced from polyols using isocyanate as curing agent, such as a polymeric methylene diphenyl diisocyanate (p-MDI). In one embodiment, the reactivity of the polyol may be adjusted using a catalyst to match the reactivity of castor oil. Suitable catalysts are well known in the art, and may include amine catalysts or other catalysts commonly used in PU production. In another embodiment, the reactivity of polyols may be adjusted by generating some proportion of primary hydroxyl groups in the hydroxylation step. This can be achieved by using di-alcohols or mixture of mono- and di-alcohols in the epoxy ring opening reaction. In this way, a controllable proportion of primary and secondary hydroxyl groups result on the side chain(s). It is known that the reactivity of the primary alcohols towards diisocyanates are higher compared to secondary hydroxyl groups.

EXAMPLES

The following examples are intended to be illustrative of specific embodiments of the claimed invention, and not limiting thereof, unless explicitly claimed in a limiting manner.

Epoxidation.

Controlled partial epoxidation of oil was carried out using in-situ generated performic acid from formic acid and hydrogen peroxide. The oil was either camelina oil or a mixture of camelina oil and flaxseed oil. The molar ratio of reactants was selected such that double bonds present in the oil:hydrogen peroxide:formic acid=1.0.1.5:0.25. Although the limited amount of acid slows the epoxidation reaction down, this condition is desirable to avoid epoxy ring opening by the acid and acid-generated nucleophile. An excess of $H_2O_2$ is desirable, partly to compensate for any loss or decomposition of peroxide during the epoxidation at elevated temperatures. The epoxidation process was carried out using a 22 L glass reactor equipped with a bottom drain, a water jacket and attached to a recirculating liquid cooler/heater (Julabo F25, Julabo USA, Inc.). The desired amount of oil (~2000 g) was added at a temperature of 25° C. The required amounts of aqueous $H_2O_2$ solution (35%) are then loaded into the vessel and the mixture stirred vigorously with an overhead mechanical stirrer (RZR 2021, Heidolph) (350±10 rpm) to form a homogenous mixture before proceeding with addition of formic acid. Then, formic acid (85% aqueous solution) is added dropwise through the addition funnel into the reactor at an addition rate of ~10 g/min. After the complete addition of formic acid to the mixture, the temperature of the reaction is increased slowly up to the desired epoxidation temperature of 60° C., while carefully monitoring temperature for possible rise due to the exothermicity of reaction. Uncontrolled rise in reaction temperature is an important safety concern requiring immediate and efficient quenching of the reaction. Depending on the planned epoxide oxirane content, the total epoxidation time of camelina oil was varied over a period of several hours. Many batches of epoxides were prepared, differing in their oxirane content and consequently also differing in their remaining iodine value (IV). As examples, Table 1 demonstrates the change of IV and oxirane oxygen content (OOC) for camelina oil and for camelina and flax oil mixtures over epoxidation time. Epoxide oxirane oxygen content was analyzed using ASTM standards (ASTM D1652-11E1).

Figure 2:
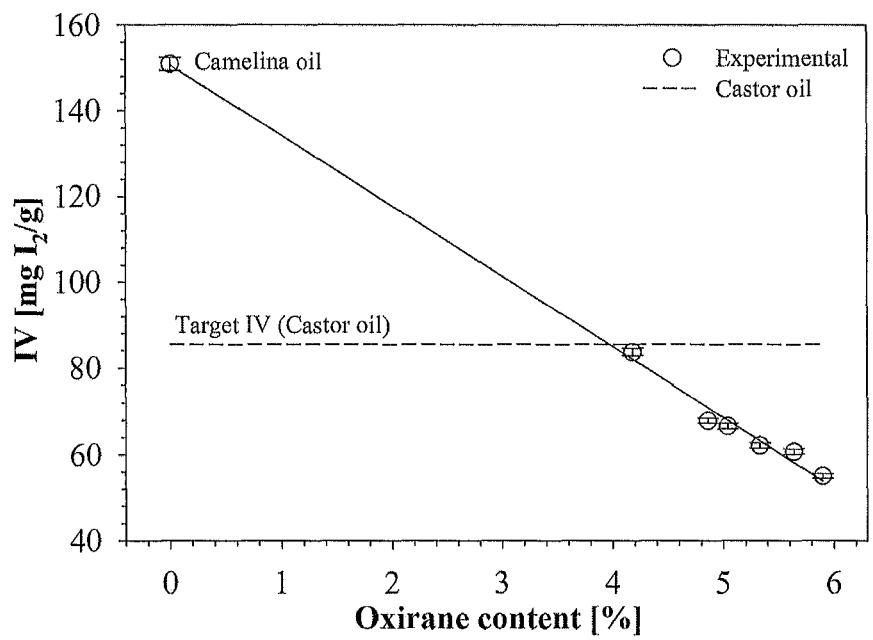
FIG. 2 shows the change of iodine value (IV) and oxirane oxygen content (OOC) for the camelina oil over epoxidation time.

FIG. 2 demonstrates the change of iodine value (IV) and oxirane oxygen content (OOC) for camelina oil (Examples 1-6 from Table 1) over epoxidation time. As described in the examples which follow, several batches of partially epoxidized camelina oil were prepared, differing with the amount of oxirane content, and consequently with different remaining IV. As epoxidation progresses, the oxirane content increases and the iodine value of camelina oil decreases.

Hydroxylation

Epoxy ring opening reactions were carried out to make polyols using the partially epoxidized oils made as described above.

An amount of partially epoxidized oil with desired OOC was loaded into a 22 L jacketed glass reactor equipped with a bottom drain, at a temperature of 60° C., while mixing at 350±10 rpm. After the temperature of the partially epoxidized oil was equilibrated at 60° C., an amount of monoalcohol was added into the reactor, in a ratio of monoalcohol to the controlled partially epoxidized TAG oil ranging from between about 1:0.3 to about 1:1 by weight. In one embodiment, the mixture was agitated as the hydroxylation reaction proceeded for between about 3.0 hours to about 24 hours, preferably from 3.0 hours to about 5.0 hours. About 10 wt % (to the controlled partially epoxidized oil) of heterogeneous solid catalyst (Amberlyst™ 15, dry) was then added into the mixture, and the epoxy ring opening process was continued for several hours. After complete epoxy ring opening (OOC<0.02%), the solid catalyst was removed by filtration and the polyols were concentrated from methanol by vacuum evaporation. The recovered methanol was then reused in further reactions.

Figure 3:
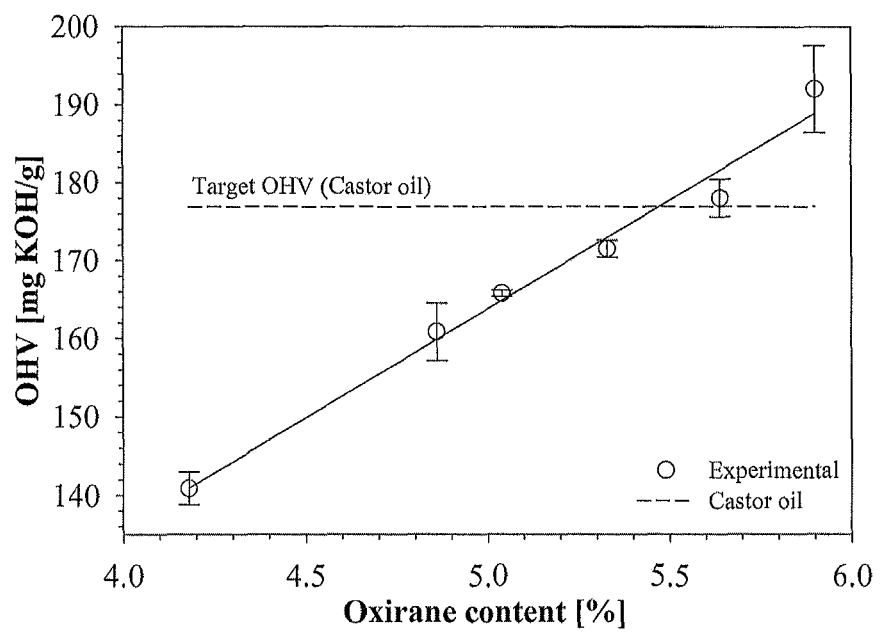
FIG. 3 shows the change of hydroxyl value with the change of oxirane content in the partially epoxidized TAG oil.

FIG. 3 demonstrates the change of hydroxyl value with the change of oxirane content in the input partially epoxidized oil. The hydroxyl value of castor oil which is about 177 mg KOH/g is shown. As may be seen, increased oxirane content leads to increased hydroxyl value.

Figure 4:
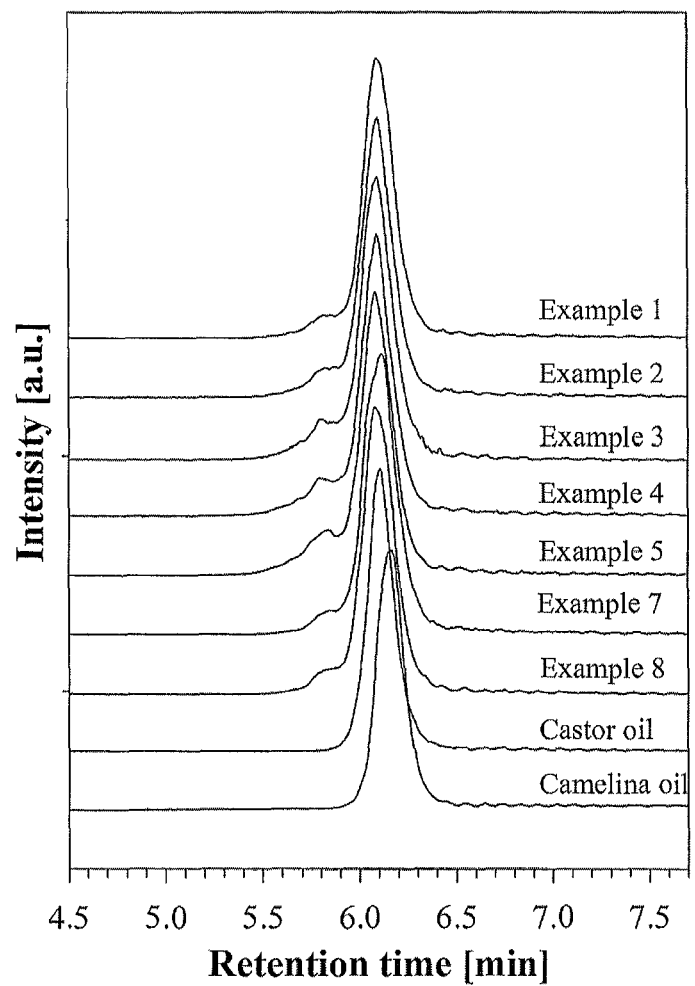
FIG. 4 shows GPC chromatograms of the examples presented in Table 1 demonstrating the mainly monomeric TAG structure of the polyols.

Analysis of the physical properties of the resulting polyols were evaluated using variety of tools. The viscosity of polyol was measured with TA Instruments AR 2000 Rheometer. The moisture content of the polyols was determined by Karl-Fisher titration using Barnstead/Thermolyne Aquametry II Apparatus. The iodine value (IV) of the polyols were measured according to ASTM standards (D 5554-95 (R 2001)). The hydroxyl value of the polyols were measured using ASTM standard methods (ASTM D 1957-86 (R 2001); ASTM E1899-08) and in-house developed Fourier transform infrared (FTIR) method. The formation of oligomeric structures, if any, were analyzed using gel permeation chromatography (GPC) using a mobile phase of tetrahydrofuran and an evaporative light scattering detector (FIG. 4). It can be seen in FIG. 4 that the polyols contain only small amounts of dimers and no higher oligomers. The dimer content of the polyols is found to be always less than 15% but in most cases less than 10%. It is also evident from FIG. 4 that the GPC monomer peak for the polyols (Examples 1-8) is indistinguishable from that of castor oil, whereas the starting camelina oil has a lower molecular weight and elutes at a slightly longer retention time (FIG. 4).

Example 1

900 g of partially epoxidized camelina oil with oxirane content of 4.18% was loaded into the reactor set to a temperature of 60° C., while mixing at 350±10 rpm. After the temperature of the controlled partially epoxidized oil is equilibrated at 60° C., methanol (900 g) was added into the reactor. About 10 wt % (90 g) of heterogeneous solid catalyst (Amberlyst™ 15, dry) was then added into the mixture. The epoxy ring opening process continued for 4.5 hours. After complete epoxy ring opening, the solid catalyst was removed by filtration and the polyols were concentrated from methanol by vacuum evaporation. The properties of a polyol produced in this way are given in Table 1.

Example 2

900 g of partially epoxidized camelina oil with oxirane content of 4.86% was loaded into the reactor set to a temperature of 60° C., while mixing at 350±10 rpm. After the temperature of the controlled partially epoxidized oil is equilibrated at 60° C., the required amount of methanol (900 g) is added into the reactor. About 10 wt % (90 g) of heterogeneous solid catalyst (Amberlyst™ 15, dry) was then added into the mixture. The epoxy ring opening process continued for 4.5 hours. After complete epoxy ring opening, the solid catalyst was removed by filtration and the polyols were concentrated from methanol by vacuum evaporation. The properties of a polyol produced in this way are given in Table 1.

Example 3

3000 g of partially epoxidized camelina oil with oxirane content of 5.04% was loaded into the reactor set to a temperature of 60° C., while mixing at 350±10 rpm. After the temperature of the controlled partially epoxidized oil is equilibrated at 60° C., the required amount of methanol (3000 g) is added into the reactor. About 10 wt % (300 g) of heterogeneous solid catalyst (Amberlyst™ 15, dry) was then added into the mixture. The epoxy ring opening process continued for 4.5 hours. After complete epoxy ring opening, the solid catalyst was removed by filtration and the polyols were concentrated from methanol by vacuum evaporation. The properties of a polyol produced in this way are given in Table 1.

Example 4

900 g of partially epoxidized camelina oil with oxirane content of 5.33% was loaded into the reactor set to a temperature of 60° C., while mixing at 350±10 rpm. After the temperature of the controlled partially epoxidized oil is equilibrated at 60° C., the required amount of methanol (900 g) is added into the reactor. About 10 wt % (90 g) of heterogeneous solid catalyst (Amberlyst™ 15, dry) was then added into the mixture. The epoxy ring opening process continued for 5 hours. After complete epoxy ring opening, the solid catalyst was removed by filtration and the polyols were concentrated from methanol by vacuum evaporation. The properties of a polyol produced in this way are given in Table 1.

Example 5

700 g of partially epoxidized camelina oil with oxirane content of 5.64% was loaded into the reactor set to a temperature of 60° C., while mixing at 350±10 rpm. After the temperature of the controlled partially epoxidized oil is equilibrated at 60° C., the required amount of methanol (700 g) is added into the reactor. About 15 wt % (105 g) of heterogeneous solid catalyst (Amberlyst™ 15, dry) was then added into the mixture. The epoxy ring opening process continued for 4.5 hours. After complete epoxy ring opening, the solid catalyst was removed by filtration and the polyols were concentrated from methanol by vacuum evaporation. The properties of a polyol produced in this way are given in Table 1.

Example 6

2000 g of partially epoxidized camelina oil with oxirane content of 5.90% was loaded into the reactor set to a temperature of 60° C., while mixing at 350±10 rpm. After the temperature of the controlled partially epoxidized oil is equilibrated at 60° C., the required amount of methanol (2000 g) is added into the reactor. About 10 wt % (200 g) of heterogeneous solid catalyst (Amberlyst™ 15, dry) was then added into the mixture. The epoxy ring opening process continued for 5.5 hours. After complete epoxy ring opening, the solid catalyst was removed by filtration and the polyols were concentrated from methanol by vacuum evaporation. The properties of a polyol produced in this way are given in Table 1.

Example 7

900 g of partially epoxidized camelina oil and flaxseed oil mixture (55/45 by weight) with oxirane content of 4.94% was loaded into the reactor set to a temperature of 60° C., while mixing at 350±10 rpm. After the temperature of the controlled partially epoxidized oil was equilibrated at 60° C., the required amount of methanol (900 g) was added into the reactor. About 10 wt % (90 g) of heterogeneous solid catalyst (Amberlyst™ 15, dry) was then added into the mixture. The epoxy ring opening process continued for 5 hours. After complete epoxy ring opening, the solid catalyst was removed by filtration and the polyols were concentrated from methanol by vacuum evaporation. The properties of a polyol produced in this way are given in Table 1.

Example 8

900 g of partially epoxidized camelina oil and flaxseed oil mixture (55/45 by weight) with oxirane content of 5.55% was loaded into the reactor set to a temperature of 60° C., while mixing at 350±10 rpm. After the temperature of the controlled partially epoxidized oil was equilibrated at 60° C., the required amount of methanol (900 g) was added into the reactor. About 10 wt % (90 g) of heterogeneous solid catalyst (Amberlyst™ 15, dry) was then added into the mixture. The epoxy ring opening process continued for 5 hours. After complete epoxy ring opening, the solid catalyst was removed by filtration and the polyols were concentrated from methanol by vacuum evaporation. The properties of a polyol produced in this way are given in Table 1.

time of polyol with no catalyst was longer than that of castor oil, but it was possible to match the castor oil gelation time with an addition of a small amount (up to 0.3 wt %) of catalyst. The gelation times of different systems are shown in the figure near respective curves.

Figure 6:
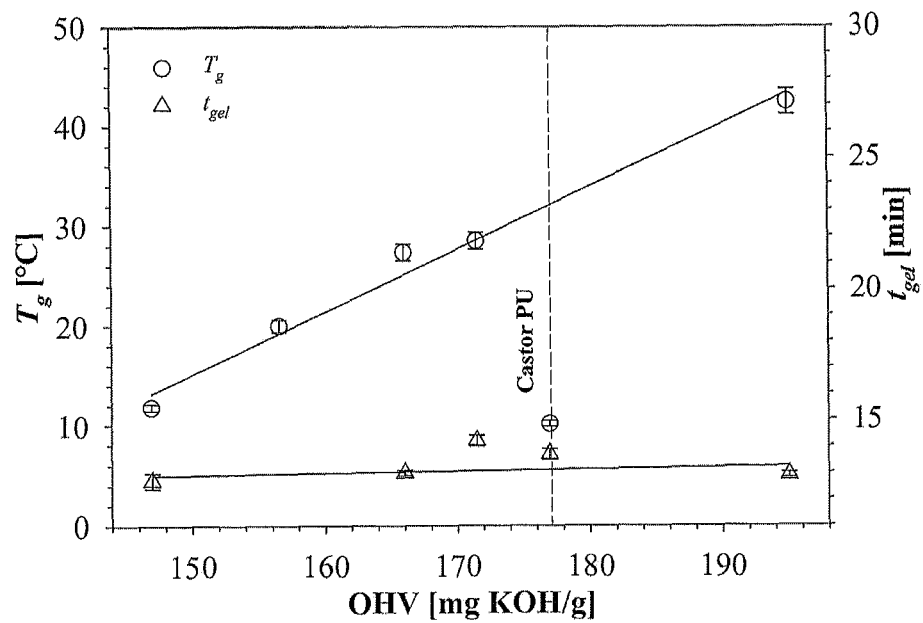
FIG. 6 shows glass transition temperatures ($T_g$) and gelation times ($t_{gel}$) of polyurethanes produced from select polyols with different hydroxyl functionality presented in Table 1. The $T_g$ and $t_{gel}$ of castor oil based PU under identical conditions are highlighted with vertical dashed line.

The glass transition temperatures ($T_g$) of the polyurethanes prepared from castor oil and from polyols were measured and compared. FIG. 6 shows the $T_g$ and $t_{gel}$ measured by dynamic scanning calorimeter (DSC Q100, TA Instruments) for castor oil and polyols with different hydroxyl functionalities and with their reactivities adjusted via catalyst addition to give similar $t_{gel}$ values. It is clear from this figure that the $T_g$ of PU does not depend on the catalyst amount but depends on OHV of polyols. The polyurethane made from the polyol produced from the in the examples above demonstrated significantly higher Tg compared to castor oil at similar gelation times, which could be beneficial in certain applications.

TABLE 1

Properties of the castor oil replacement polyols, castor oil and camelina oil and camelina and flax oil mixtures.

| Examples | Epoxide oxirane oxygen content [%] | Hydroxyl # [mg KOH/g] | Acid # [mg KOH/g] | Viscosity @25° C. [Pa · s] | Iodine Value [g I₂/100 g] | Moisture [%] | Dimers (%, GPC) |
|---|---|---|---|---|---|---|---|
| Example 1 | 4.18 | 140.9 ± 0.1 | 0.6 ± 0.1 | 0.63 ± 0.01 | 81.3 | 0.04 ± 0.01 | 5.7 |
| Example 2 | 4.86 | 162.9 ± 1.8 | 0.7 ± 0.1 | 1.17 ± 0.01 | 67.5 | 0.04 ± 0.01 | 7.5 |
| Example 3 | 5.04 | 165.8 ± 0.4 | 0.5 ± 0.1 | 1.23 ± 0.01 | 66.6 | 0.04 ± 0.01 | 9.3 |
| Example 4 | 5.33 | 171.5 ± 1.1 | 0.6 ± 0.1 | 1.66 ± 0.01 | 62.1 | 0.03 ± 0.01 | 11.4 |
| Example 5 | 5.64 | 178.0 ± 2.4 | 0.7 ± 0.1 | 2.07 ± 0.01 | 60.7 | 0.04 ± 0.01 | 13.4 |
| Example 6 | 5.90 | 194.7 ± 5.8 | 0.5 ± 0.1 | 2.52 ± 0.01 | 55.2 | — | — |
| Example 7 | 4.94 | 162.3 ± 2.4 | 0.6 ± 0.1 | 0.91 ± 0.01 | 85.0 | 0.04 ± 0.01 | 4.6 |
| Example 8 | 5.55 | 188.6 ± 5.9 | 0.6 ± 0.1 | 1.60 ± 0.01 | 70.6 | 0.05 ± 0.01 | 6.1 |
| Castor Oil | — | 176.9 ± 0.2 | — | 0.7 ± 0.01 | 85.5 | — | — |
| Camelina Oil | — | — | — | 0.061 ± 0.001 | 150.9 | — | — |

In Table 1, the acid value is equal to the mass of potassium hydroxide (KOH) in milligrams that is required to neutralize one gram of polyol. A lower acid value is preferred since this results in fewer unwanted side reactions when the polyol is used to make polyurethanes, and also so that the polyol resembles refined castor oil, for example for use in personal care or cosmetic formulations. The dimer percentage values are based on uncorrected peak areas from GPC-ELSD and hence are likely overestimates due to the lower response factors for low molecular weight components.

Polyurethanes

Figure 5:
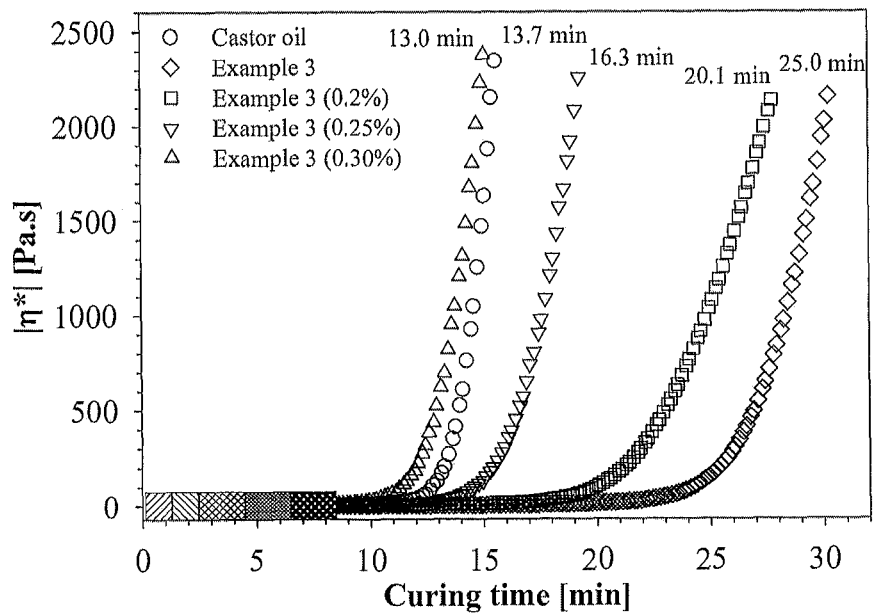
FIG. 5 shows gelation process of the polyols from Example 3 presented in Table 1, demonstrating how adjustment to the reactivity of a polyol towards polymeric methylene diphenyl diisocyanate (p-MDI) to produce polyurethanes, can be achieved by the addition of a controlled amount of catalyst.

To determine the reactivity of polyols in making PU, and to compare the reactivity of the same with castor oil, a series of real-time curing experiments using p-MDI have been carried out in a rheometer (Advanced Rheometer AR 2000, TA Instruments). Gelation times (as an indicative of reactivity) of polyols with p-MDI at a ratio of —OH/—NCO=1.0/1.2 were determined performing isothermal (70° C.) time sweep tests with 25-mm disposable parallel plates under controlled displacement at a frequency of 1 Hz. FIG. 5 shows the complex viscosity against curing time for the PU series made from Example 3 presented in Table 1 (with addition of catalyst) and for castor oil. The patterned boxes in the graph indicates sample preparation protocol including 1 min of polyol mixing with isocyanate at room temperature; 1 min of degassing in vacuum oven at 70° C.; ~2 min of sample transfer from oven to rheometer; ~2 min of preconditioning of the sample to 70° C.; 2 min of equilibrium conditioning of sample at 70° C. prior to measurements of viscoelastic properties. FIG. 5 demonstrates that the gelation Definitions and Interpretation As used herein, the term "fatty acid" means a carboxylic acid consisting of a hydrocarbon chain and a terminal carboxyl group. In addition, "fatty acid" refers to both free fatty acids and bound fatty acids. Bound fatty acids are fatty acid residues that are attached to other molecules, including any of those occurring as esters in fats and oils. The term "triacylglycerol" means an ester of three fatty acids and glycerol, which is the chief constituent of fats and oils.

As used herein, the term "epoxidation" means a chemical reaction in which an oxygen atom is joined to an olefinically unsaturated molecule to form a cyclic, three-membered ether. The products of epoxidation are known as oxirane compounds or epoxides.

As used herein, the term "oxirane oxygen content" or "OOC" means the weight percent of oxirane oxygen in a molecule, and may be measured by methods described in ASTM D 1652-11E1.

As used herein, the term "hydroxyl value" or "OHV" means the number of milligrams of potassium hydroxide required to neutralize the acetic acid taken up on acetylation of one gram of a chemical substance that contains free hydroxyl groups, and may be measured by methods described in ASTM E222-10. The term "acid value" means the number of milligrams of potassium hydroxide required to neutralize polyols produced by an embodiment of the present invention.

As used herein, the term "iodine value" means a measure of the unsaturated fatty acid content of a product. Iodine value may be measured by methods described in ASTM D 5554-95 (R 2001).

As used herein, the term "transesterification" means a process of exchanging the organic group R" of an ester with the organic group R' of an alcohol.

As used herein, the term "hydroxylation" means a chemical process that introduces a hydroxyl group (—OH) into an organic compound.

As used herein, the term "monoalcohol" or "monohydric alcohol" means an alcohol having one hydroxyl group. As used herein, the term "diol" or "dihydric alcohol" means an alcohol having two hydroxyl groups. As used herein, the term "triol" or "trihydric alcohol" means an alcohol having three hydroxyl groups.

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

REFERENCES

The following references are incorporated herein by reference (where permitted) as if reproduced in their entirety. All references are indicative of the level of skill of those skilled in the art to which this invention pertains.

Curtis, J et al. Polyol synthesis from fatty acids and oils. U.S. Pat. No. 9,216,940

Holser, R. A. (2008) Transesterification of epoxidized soybean oil to prepare epoxy methyl esters. *Industrial Crops and Products* 27(3):130-132.

Strukul, G. Catalytic Oxidations with Hydrogen Peroxide as Oxidant, Kluwer Academic Publishers, The Netherlands, 1992.

What is claimed is:

1. A method for the preparation of polyols from an unsaturated triacylglycerol (TAG) oil, consisting essentially of the steps of:
   (a) partially epoxidizing the unsaturated TAG oil, having an iodine value greater than about 120, with an acid and an oxidizing agent to obtain a partially epoxidized TAG oil which is still unsaturated; and
   (b) hydroxylating the partially epoxidized TAG oil using an monoalcohol and an acid catalyst to obtain hydroxylated and unsaturated TAG polyols, comprising monomeric and dimeric, but not oligomeric, TAG polyols.

2. The method of claim 1, wherein the unsaturated TAG oil comprises camelina oil, canola oil, high oleic canola oil, sunflower oil, juvenile canola oil, flaxseed oil, camelina oil, solin oil, yellow mustard oil, brown mustard oil, oriental mustard oil, palm oil olein, or palm oil, soy oil, high erucic acid rapeseed oil, hemp oil, safflower oil, corn oil, olive oil, cottonseed oil, peanut oil, nut oils, algal oils, fish oils, or mixtures thereof.

3. The method of claim 2, wherein the unsaturated fatty acid comprises camelina oil or a mixture of camelina oil and flaxseed oil.

4. The method of claim 1, wherein the acid comprises formic acid or acetic acid.

5. The method of claim 1, wherein the oxidizing agent comprises hydrogen peroxide.

6. The method of claim 1, wherein the partially epoxidized TAG oil is extracted using an organic solvent and dried.

7. The method of claim 1, wherein the acid catalyst comprises a heterogeneous macroreticular ion exchange resin.

8. The method of claim 1, wherein the ratio of the monoalcohol to the partially epoxidized TAG oil ranges from between about 1:0.3 to about 1:1 by weight.

9. The method of claim 8, wherein the monoalcohol comprises methanol or ethanol.

10. The method of claim 1, wherein hydroxylation is conducted for between about 3.0 hours to about 24 hours, or from 3.0 hours to about 12 hours, or from 3.0 hours to about 5.0 hours.

11. The method of claim 1 wherein epoxidation of the unsaturated TAG oil is stopped when the partially epoxidated TAG oil has an OOC ranging from about 3.0% to about 6.0%.

12. The method of claim 11 wherein the epoxidation of the unsaturated TAG oil is stopped when the TAG oil has an OOC ranging from about 4.0% to about 5.5%.

13. The method of claim 1 wherein the TAG oil is mixed with the oxidizing agent at a temperature of between about 20° to about 40° C.

14. The method of claim 13 wherein the acid is added in small portions to the mixture of TAG oil and oxidizing agent, and the temperature is gradually increased to about 40° C. to about 80° C., after or during addition of the acid.

15. The method of claim 1 wherein the acid catalyst is added to a mixture of the partially epoxidized TAG oil and a monoalcohol at a temperature of about 40° C. to about 80° C.

16. The method of claim 1 wherein a molar ratio of acid to TAG oil double bonds is less than 1:1 and/or a molar ratio of oxidizing agent to TAG oil double bonds is greater than 1:1.

17. The method of claim 16 wherein a molar ratio of TAG oil double bonds:oxidizing agent:acid is about 1.0:1.5:0.25.

18. A composition comprising hydroxylated and unsaturated monomeric and dimeric, but not oligomeric, triacylglycerol polyols having the following properties:
   (a) a hydroxyl value ranging from about 110 mgKOH/g to about 210 mgKOH/g;
   (b) a viscosity of between about 0.4 Pa·s to about 2.5 Pa·s;
   (c) an iodine value of between about 55 to about 90; or
   (d) an acid value of less than about 1.0 mg KOH/g.

19. The composition of claim 18, wherein the polyols have one or more of the following properties:
   (a) a hydroxyl value of between about 150 mgKOH/g to about 200 mgKOH/g;
   (b) a viscosity of between about 0.6 Pas to about 1.6 Pa·s;
   (c) an iodine value of between about 60 to about 80; or
   (d) an acid value of less than about 0.7 mg KOH/g.

20. The composition of claim 19 having less than 15% non-monomeric content.

* * * * *